United States Patent
Heske, III

(10) Patent No.: US 10,073,044 B2
(45) Date of Patent: Sep. 11, 2018

(54) SCANNER AUTOMATIC DIRTY/CLEAN WINDOW DETECTION

(71) Applicant: NCR Corporation, Duluth, GA (US)

(72) Inventor: Theodore Heske, III, Suwanee, GA (US)

(73) Assignee: NCR Corporation, Atlanta, GA (US)

( * ) Notice: Subject to any disclaimer, the term of this patent is extended or adjusted under 35 U.S.C. 154(b) by 208 days.

(21) Appl. No.: 14/279,397

(22) Filed: May 16, 2014

(65) Prior Publication Data

US 2015/0330913 A1    Nov. 19, 2015

(51) Int. Cl.
*G01N 21/94* (2006.01)
*G01N 21/88* (2006.01)
*G01N 21/958* (2006.01)
*G06K 7/00* (2006.01)

(52) U.S. Cl.
CPC ......... *G01N 21/94* (2013.01); *G01N 21/8803* (2013.01); *G01N 21/8851* (2013.01); *G01N 21/958* (2013.01); *G06K 7/0095* (2013.01); *G01N 2201/061* (2013.01); *G01N 2201/12* (2013.01)

(58) Field of Classification Search
CPC .. G01N 21/94; G01N 21/958; G01N 21/9501; G01N 21/8806; G01N 21/956; G01N 21/896; G01N 2021/945; G01N 21/8803; G01N 21/8851; G01N 21/88; G01N 2201/061; G01N 2201/12; G06K 7/0095
USPC ..................... 356/239.8, 239.7, 237.4, 237.2
See application file for complete search history.

(56) References Cited

U.S. PATENT DOCUMENTS

| 4,931,657 A | * | 6/1990 | Houston | G01N 21/86 |
| | | | | 250/225 |
| 5,278,411 A | * | 1/1994 | Popil | G01N 21/94 |
| | | | | 162/263 |
| 5,469,253 A | * | 11/1995 | Shofner | D01G 31/003 |
| | | | | 356/238.3 |
| 7,046,399 B2 | | 5/2006 | Endo | |
| 8,805,025 B2 | | 8/2014 | Chen et al. | |
| 8,983,168 B2 | | 3/2015 | Chen et al. | |
| 9,022,288 B2 | | 5/2015 | Nahill et al. | |
| 2002/0101618 A1 | * | 8/2002 | Endo | H04N 1/409 |
| | | | | 358/3.22 |

(Continued)

FOREIGN PATENT DOCUMENTS

| CN | 103366358 A | 10/2013 | |
| CN | 103377509 A | 10/2013 | |
| JP | 10-294870 | * 11/1998 | G06T 1/00 |

OTHER PUBLICATIONS

AIPN English translation of JP document Hiroyuki (JP 10-294870 (Ricoh—1998)).*

(Continued)

*Primary Examiner* — Mohamed K Amara
(74) *Attorney, Agent, or Firm* — Schwegman, Lundberg & Woessner

(57) ABSTRACT

An image from a window of a scanner is taken and analyzed to determine whether the image is relevant to dirt or debris on the window. When the image is relevant to dirt or debris, the size and amount of the dirt or debris is compared to a threshold and when the threshold is exceeded an alert is raised to have the window cleaned of the dirt or debris.

6 Claims, 4 Drawing Sheets

(56) References Cited

U.S. PATENT DOCUMENTS

| | | | | |
|---|---|---|---|---|
| 2003/0090742 A1* | 5/2003 | Fukuda | ............ | H04N 1/04 |
| | | | | 358/448 |
| 2004/0240736 A1* | 12/2004 | Karidi | ............ | G06K 9/00456 |
| | | | | 382/176 |
| 2007/0295814 A1* | 12/2007 | Tanaka | ............ | G06K 7/10722 |
| | | | | 235/454 |
| 2011/0241876 A1 | 10/2011 | Kearney | | |
| 2013/0177246 A1* | 7/2013 | Stokes | ............ | G06K 9/00456 |
| | | | | 382/182 |
| 2014/0061305 A1* | 3/2014 | Nahill | ............ | G06K 7/0095 |
| | | | | 235/438 |
| 2014/0184636 A1* | 7/2014 | Kelly | ............ | H04N 19/85 |
| | | | | 345/619 |
| 2014/0234994 A1* | 8/2014 | Abe | ............ | G01N 21/6489 |
| | | | | 438/16 |
| 2015/0213579 A1* | 7/2015 | Alacoque | ............ | G06T 3/4053 |
| | | | | 382/300 |

OTHER PUBLICATIONS

European Search Report issued in European Patent Application EP15163740.2 dated Oct. 8, 2015.

\* cited by examiner

SCANNER AUTOMATIC DIRTY/CLEAN WINDOW DETECTION

BACKGROUND

An imaging bar code scanner operates in environments where it is constantly exposed to dirt, debris, and other contaminants. Some of this dirt, etc., will get deposited on one or more of the scanner's optical windows, and will necessarily degrade the quality of images acquired by that scanner. Degraded image quality, in turn, naturally degrades performance of the scanning equipment.

In an imaging bar code scanner, light traverses one or more optical components on its way from the imaged object to one or more image sensors. Optical components perform at their best when they are free of dirt, grease, and any other contaminants that may scatter, absorb, or diffract light as it travels from the object to the sensor. Typical operations of a bar code scanner in a Point-Of-Sale (POS) system constantly expose parts of the scanner to dirt, etc., from the environment, some of which may be deposited on one or more of the scanner's optical components. The overall effect of the dirt then is that it may obscure the image in the places where the dirt is interposed between the object and the sensor. An additional complicating factor is that the dirt may appear different to the image sensor, depending on whether the dirt is back-lit by illumination from the environment, or whether the dirt is front-lit by illumination coming from the scanner itself. In both cases the dirt decreases the ability of a bar code scanner to perform its primary function, which relies upon the acquisition of images that are essentially free from optical defects, including defects caused by dirt, etc., in the optical path.

It is therefore desirable to have an imaging bar code scanner that can detect when dirt is obscuring the image. It is also desirable to have an imaging bar code scanner that can alert an operator that the scanner's optical components need cleaning. Furthermore, it is desirable to have a scanner that can detect when it is clean again so that the operator alert can be set to a non-alerting state. Finally, it is desirable to have a scanner that is equally effective at detecting both back-lit and front-lit dirt.

SUMMARY

In various embodiments, methods and a system for automatic dirty/clean window detection are provided.

According to an embodiment, a method for automatic dirty/clean window detection of a scanner is provided. Specifically, an image is obtained from a scanner and the image is sampled for detection of dirt or debris. Next, a determination is made whether a window of the scanner is dirty or clean based on the sampled image.

DETAILED DESCRIPTION

Figure 1:
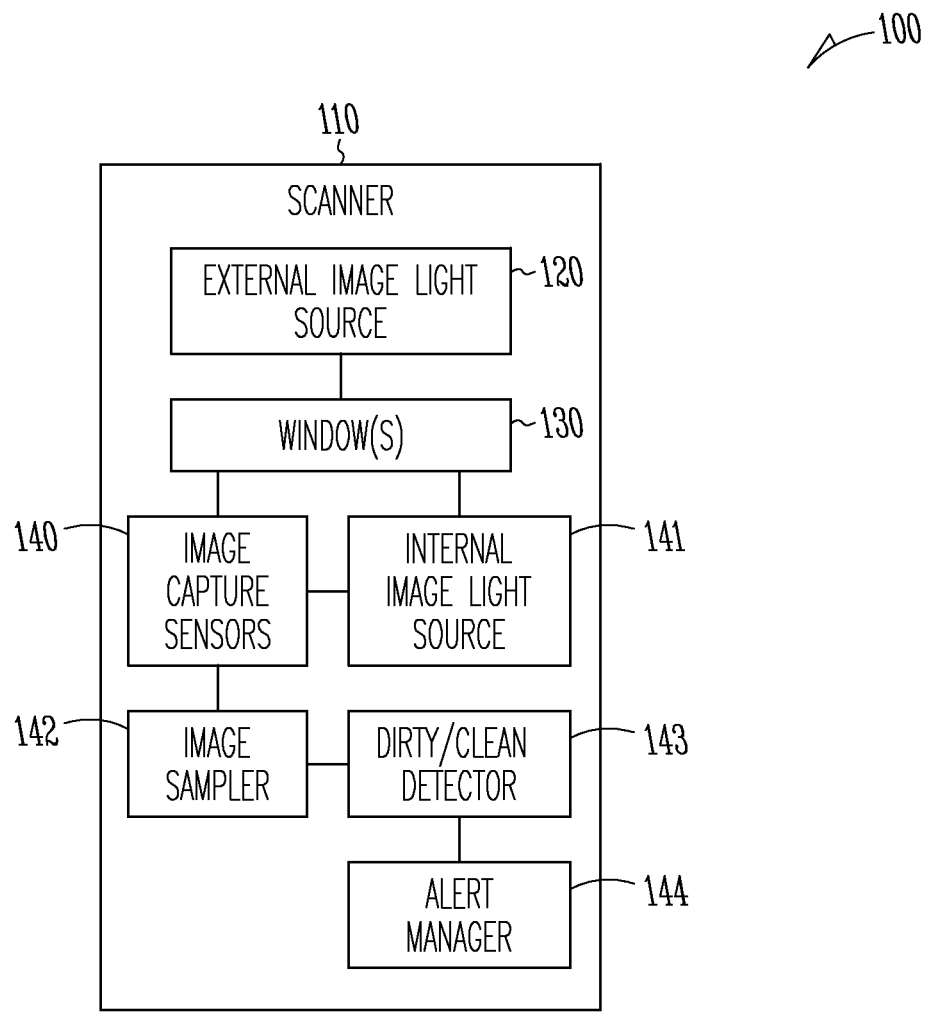
FIG. 1 is a diagram illustrating components of an optical scanner that automatically detects whether window(s) of the optical scanner are dirty or clean, according to an example embodiment.

FIG. 1 is a diagram 100 illustrating components of an optical scanner 110 that automatically detects whether window(s) 130 of the optical scanner 110 are dirty or clean, according to an example embodiment. It is to be noted that the optical scanner 110 is shown schematically in greatly simplified form, with only those components relevant to understanding of this embodiment being illustrated. The same situation may be true for the various other illustrated components of the optical scanner 110.

Furthermore, the various components (that are identified in the FIG. 1) are illustrated and the arrangement of the components is presented for purposes of illustration only. It is to be noted that other arrangements with more or less components are possible without departing from the teachings of automatic dirty/clean window detection, presented herein and below.

Furthermore, methods and system presented herein and below for automatic dirty/clean window detection may include all or some combination of the components shown with the diagram 100. The methods are programmed as executable instructions in memory and/or non-transitory computer-readable storage media and executed on one or more processors associated with the components/devices.

Specifically, the diagram 100 permits an optical scanner 110 to automatically determine when windows 130 of the optical scanner 110 are to be considered dirty or clean. The details of this approach in view of the components, within the diagram 100, are now presented with reference to an embodiment of the FIG. 1 within an optical scanner 110.

However, before discussion of the diagram 100 is presented, it is to be noted that the methods and system presented herein are not limited to Point-Of-Sale (POS) installations; that is, any scanner environment or system (associated with any Self-Service Terminal (SST), kiosk, vending machine, check-in and/or check-out terminal, such as those used in retail, hotel, car rental, healthcare, or financial industries, etc.) can benefit from the teachings presented herein.

The optical scanner 110 includes an external image light source 120 (optional), one or more windows 130, image capture sensors 140, an internal image light source 141, an image sampler 142, a dirty/clean detector 143, and an alert manager 144.

In an embodiment, the optical scanner 110 is integrated into a Self Service checkout station operated by a customer.

In an embodiment, the optical scanner 110 is integrated into a POS checkout station operated by a cashier.

The optical scanner has an outermost portion (at least one side of the windows 130), which is in contact with the environment, and an internal portion (inside portion of at least one window 130 and components 140-144), which is internal to the optical scanner 110 (it is noted that in an embodiment, the optical scanner 110 is a barcode scanner 110). The outermost portion of the optical scanner 110 may be expected to be subjected to various sources of dirt, debris, and contamination from the environment, and some of this dirt, etc., may adhere to any portion of the outermost portion (outside portion of at least one window 130). The internal portion of the optical scanner 110 may be sealed to a meaningful degree against the infiltration of dirt, debris, etc.

The optical scanner 110 (hereinafter "scanner 110") has an optical system that provides a substantially focused image of an object to a two-dimensional (2D) image sensor 140. It should be appreciated that a scanner 110 may have one or more image sensors 140 and that each of these may be provided with a substantially focused image of one or more objects by one or more optical systems. It should also be appreciated that a scanner 110 may obtain images of the same object from multiple viewing angles.

The 2D image sensor 140 has a regularly spaced grid of sensor elements such that an optical image that is captured is transformed by the sensor 140 into an array of pixel values, one pixel value corresponding to each sensor element and recording data such as light intensity and color. In this way a 2D image sensor 120 may convert the image provided by the optical system into an array of pixel values that may then be manipulated mathematically.

An object (such as a barcode on a produce being scanned), which is outside the scanner, may be imaged by the scanner 110 by passing light from the object (perhaps by using an external image light source 120), through an optical window 130 in the outermost portion of the scanner, through the remainder of the optical system inside the scanner 110, to one or more image sensors 140. Depending on the design of the scanner 110, there may be multiple optical windows 130 passing light from the object to one or more optical systems and then on to one or more image sensors 140. It is clear that dirt, etc., from the environment may adhere to any or all of the optical windows 130 of a scanner 110 and that the dirt may negatively impact image quality as a result.

The automatic detection of a dirty or clean window 130 for the scanner 110 is achieved by one or more of the three processing approaches, each of which are performed by the image sampler 142 and/or the dirty/clean detector 143 (implemented as executable instructions as one or more software modules that execute on one or more processors of the scanner 110).

First Approach

The first approach is as follows:

1) capture an image from the sensor 140 and transform it into an array of pixels, in which the value of each pixel is at least a representation of the intensity of light received at that pixel location;

2) set a Speckle Count equal to zero;

3) then for each pixel of the image;

3a) sample from the captured image a 3×3 array of pixels with the current pixel at the center and the eight nearest neighbor pixels surrounding the center pixel;

3b) compare the value of the center pixel to the value of each of the 8 nearest neighbor pixels;

3c) if the center pixel is greater than all eight neighboring pixels, or, the center pixel is less than all eight neighboring pixels then increment the Speckle Count; and, 4) the Speckle Count is now proportional to the amount of dirt that is on the window 130.

For the first approach, the 3×3 array of pixels may be visualized as follows, in which pC represents the center pixel, and p1-p8 represent the 8 nearest neighbor pixels:

|    |    |    |
|----|----|----|
| P1 | P2 | P3 |
| P4 | PC | P5 |
| P6 | P7 | P8 |

For sake of more clearly describing the processing of 3b and 3c listed above, suppose all eight neighboring pixels are sorted from p1 to p8 from lowest value to highest value, such that pL is equal to the value of the lowest value pixel, and pH is equal to the value of the highest value pixel. So, processing steps 3b and 3c (listed above) become: IF (pC<pL) OR (pC>pH) THEN Speckle_Count=Speckle_Count+1.

It is noted that the step of sorting p1 through p8 is done strictly for purposes of finding both the highest and lowest pixel values from the example eight pixel neighborhood. It is, however, sufficient to sort p1 through p8 for this purpose but is not required. What is necessary is to find the minimum and maximum pixel values, which can be accomplished without doing a full sort on p1 through p8. Avoiding a full sort, in favor of simply determining the minimum and maximum pixel values from p1 through p8 may lead to a run time processing improvement.

In an embodiment, the first approach is not used on edges of an image due to possible side effects of doing the same. For example, the uppermost left hand corner pixel of an image does not have a full eight neighborhood of pixels in the captured image (because pixels p1, p2, p3, p4, and p6 are off of the edge of the image and don't exist as pixels). Edge effects are completely eliminated by processing the first approach on just the subset of pixels for which a full eight pixel neighborhood can be selected.

Illumination from outside the scanner 110 (via the optional external image light source 120) will tend to make dirt on the window appear dark compared to the surrounding pixels as the dirt may block the light from the image sensor 140. Illumination originating from inside the scanner 110 (via the internal image light source 141) will tend to make dirt on the window appear bright compared to the surrounding pixels as the light will be scattered back to the image sensor 140 before exiting the scanner 110. In this manner dirt may be detected regardless of the illumination configuration.

Second Approach an Enhanced Version of the First Approach

Additional flexibility and noise immunity in the first approach may be obtained, optionally, by adding a configurable pixel comparison threshold to the comparison operation done with respect to the center pixel (as discussed in the first approach above). The processing, thus augmented is as follows (note that the enhanced process, as compared to processing of the first approach, is underlined below for clarity):

1) capture an image from the sensor 140 and transform it into an array of pixels, in which the value of each pixel is at least a representation of the intensity of light received at that pixel location;

2) set a Speckle Count equal to zero;

2a) Set a pixel comparison threshold value;

3) then for each pixel of the image for which a full 8 pixel neighborhood exists:

3a) sample from the captured image a 3×3 array of pixels with the current pixel at the center and the eight nearest neighbor pixels surrounding the center pixel;

3b) compare the value of the center pixel to the value of each of the 8 nearest neighbor pixels;

3c) if the center pixel is greater than all eight neighboring pixels by more than the pixel comparison threshold value, or, the center pixel is less than all eight neighboring pixels by more than the pixel comparison threshold value then increment the Speckle Count; and, 4) the Speckle Count is now proportional to the amount of dirt that is on the window.

For sake of more easily describing the processing steps of 3b and 3c of second approach, all eight neighboring pixels are sorted from p1 to p8 from lowest value to highest value, such that pL is equal to the value of the lowest value pixel, pH is equal to the value of the highest value pixel, and pT is equal to the pixel comparison threshold value. Processing steps 3b and 3c of the second approach becomes: IF (pC<(pL−pT)) OR (pC>(pH+pT)) THEN Speckle_Count=Speckle_Count+1;

Third Approach for Multi-Resolution

The previously described speckle count accumulates counts for dirt particles that are commensurate in size with the apparent size of a single pixel. The physical size of dirt that may be deposited on a scanner will span a range of sizes. Since dirt may span a range of physical sizes it is desirable to have an approach for detecting dirt of different apparent sizes. The first and second approached (discussed above) may be adapted and enhanced to achieve this by the following third approach of down sampling the original captured image.

Supposing a captured image has a resolution of H horizontal pixels by V vertical pixels. The total number of pixels is the product H*V, and the detectable dirt has a size commensurate with the area of a single pixel. It is possible to down-sample the original H by V size image to an image that is H/2 by V/2 in size. Each 2×2 block of pixels in the original image is averaged together to yield a single pixel in the down-sampled image:

p1 p2
p3 p4==>> becomes a single pixel pM (mean of the 4 pixels)=(p1+p2+p3+p4)/4

This down-sampling scheme has 4:1 pixel ratio because for each 4 pixels in the original image a single pixel is produced in the down-sampled image.

The down-sampled image is then processed through the first approach or the second approach to produce a Speckle Count that pertains to the size scale of a single pixel in the down-sampled image, which is now 4 times larger than the size scale of dirt measured using the original image. A speckle count that is derived then from the 4:1 down-sampled image is expected to characterize dirt particles having a size that is roughly 4 times larger than a speckle count computed on the original image.

This third approach of down-sampling and then speckle counting can be applied numerous times in sequence to produce a series of down-sampled images and corresponding speckle counts that pertain to multiple size scales of dirt particles. Each time the image is down-sampled the particle size detected increases proportionally. This third approach is referred to as a multi-resolution technique, since the down-sampling produces successive images having a constant geometric ratio between images. As a result of the multi-resolution down-sampling of the original image, the speckle counts derived from each level of the down-sampled image characterize dirt particles of increasing size according to the same geometric ratio. Each speckle count is proportional to the amount of dirt that is on the window 130, that dirt being commensurate in size with the geometric area represented by the down-sampled single pixel.

To illustrate the point, consider an image that is down-sampled by 4:1 from the original image of H×V resolution. The resulting image has a resolution of H/2×V/2. If the down-sampled image is then down-sampled again by 4:1 then the resulting image has a resolution of H/4×V/4. As a result, each pixel in the H/4×V/4 double down-sampled image corresponds to square patch of 16 pixels of the original image. A speckle count that is derived then from the double down-sampled image is expected to characterize dirt particles having a size that is roughly 16 times larger than a speckle count computed on the original image.

Timing of Automatic Dirty/Clean Window Detection

It is beneficial for the scanner 110 to intelligently determine the times at which a single speckle count or a multi-resolution speckle count series may be performed. Since the goal is to characterize the state of the scanner 110 through automatic detection of clean or dirty windows 130, it is useful to avoid capturing images and computing speckle counts when either customers or cashiers are presently interacting with the POS equipment to which the scanner is integrated. For this purpose, human activity at the POS equipment may be inferred by monitoring scanner activity, weigh scale activity, and other observables at the POS equipment. For example, if the weigh scale sees a non-zero, stable weight, it is a reliable indication that the POS is in use and is therefore not the best time to capture images for the computation of speckle counts. The reading of a bar code is another reliable indication that the POS is in use and is therefore not the best time to compute speckle counts. Other indicators of the POS in-use may be derived from the POS itself. When the POS is determined to not be in-use, images may be captured and speckle counts may be computed with greater confidence.

Alerting

The alert processing is performed by the alert manager 144 (implemented as executable instructions representing software modules that execute on one or more processors of the scanner 110).

In operation, when the scanner 110 is in a clean state and not in-use, images may be captured, speckle counts may be computed, and a baseline may thereby be established for the scanner 110 when in a clean state. When subsequent speckle counts deviate from the clean state sufficiently the scanner 110 may determine that it is in a dirty state. An increase in speckle counts at a predetermined size scale, or series of size scales according to the results of a multi-resolution speckle count series (the results of processing the approaches discussed above using the image sampler 142 and/or the dirty/clean detector 143) can indicate that the scanner 110 is in a dirty state. A scanner operator may be alerted visually or audibly when the speckle counts indicate that the scanner 110 is in a dirty state by the alert manager 144. Once the scanner 110 sees speckles counts return substantially to normal the operator alert may be stopped, via the alert manager 144.

The embodiments herein have the advantage of measuring the size and amount of dirt, etc., on one or more windows 130 of an imaging bar code scanner 110 (one embodiment for the scanner 110) and using those measurements to alert an operator when the scanner 110 needs to be cleaned. A scanner 110 performs best when it is clean so operator productivity is enhanced by the embodiments herein.

These and other embodiments are now discussed with reference to the FIGS. 2-4.

Figure 2:
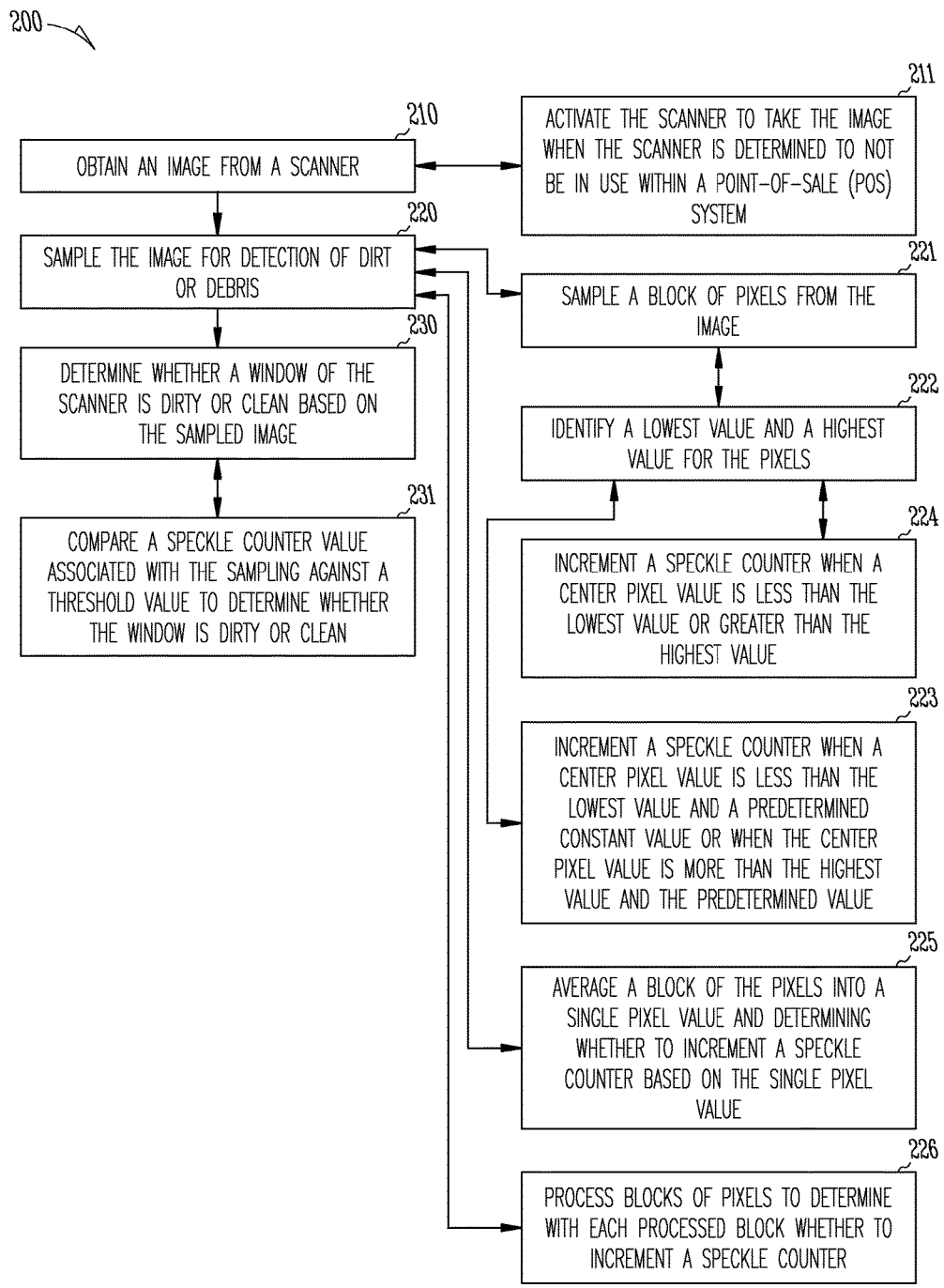
FIG. 2 is a diagram of a method for automatic dirty/clean window detection of a scanner, according to an example embodiment.

FIG. 2 is a diagram of a method 200 for automatic dirty/clean window detection of a scanner, according to an example embodiment. The software module(s) that implements the method 200 is referred to as a "scan window state manager." The scan window state manager is implemented as executable instructions programmed and residing within memory and/or a non-transitory computer-readable (processor-readable) storage medium and executed by one or more processors of a scanner. The processor(s) of the scanner that executes the scan window state manager are specifically configured and programmed to process the scan window state manager. The scan window state manager may, but does not have to have, access to a network during its processing. The network can be wired, wireless, or a combination of wired and wireless.

In an embodiment, the scanner that executes the scan window state manager is the scanner 110 of the FIG. 1.

In an embodiment, the scanner that executes the scan window state manager is a bar code scanner.

In an embodiment, the scanner that executes the scan window state manager is integrated into a checkout station operated by a cashier.

In an embodiment, the scanner that executes the scan window state manager is integrated into a self-service checkout station operated by a customer.

In an embodiment, the scan window state manager is the dirty/clean detector 143 of the FIG. 1.

In an embodiment, the scan window state manager is a combination of the image sampler 142 and the dirty/clean detector 143 of the FIG. 1.

The processing of the scan window state manager assumes that a predefined value for what is considered to be a dirty window or what is considered to be a clean window exists and is accessible to the scan window state manager. In an embodiment, this is done by using a speckle count for a known clean window of the scanner and captured when the scanner is not being operated by a customer or a cashier. The timing of that capture was discussed above and can be inferred based on the state of POS equipment to which the scanner is integrated.

At 210, the scan window state manager obtains an image from a scanner. This image is of the window where product or information is scanned from outside the environment of the scanner. Moreover, the image is obtained when no product or information is being scanned on the scanner. This allows for inspection of images taken of the window for any visible dirt and debris, which, if present, may alter the accuracy of the scanner.

According to an embodiment, at 211, the scan window state manager activates the scanner to take the image of the window when the scanner is determined to not be in use within a POS system. The situations in which the POS system can be inferred to not be in use were discussed above with reference to the FIG. 1.

At 220, the scan window state manager samples the image for detection of any dirt or debris that may be on the surface of the window.

In an embodiment, at 221, the scan window state manager samples predefined blocks of pixels from the image.

In an embodiment of 221 and at 222, the scan window state manager sorts the pixels in each block from lowest value to highest value.

In an embodiment of 222 and at 223, the scan window state manager increments a speckle counter when a center pixel value is less than the lowest value or greater than the highest value. This is an indication that the block being sampled is in fact a spec of dirt or debris on the window of the scanner.

In another embodiment of 222 and at 224, the scan window state manager increments a speckle counter when a center pixel value is less than the lowest value and a predetermined constant value or when the center pixel value is more than the highest value and the predetermined value. This is another approach to determine when the block being sampled is identified as a spec of dirt or debris present on the window of the scanner.

In an embodiment of 220 and at 225, the scan window state manager averages pixel values in each sampled to come up with a single pixel value and that single pixel value is then used for determining whether to increment a speckle counter based on the single pixel value. This was discussed above with respect to the multi-resolution approach.

In an embodiment of 220 and at 226, the scan window state manager processes the blocks of pixels to determine with each processed block whether to increment a speckle counter.

At 230, the scan window state manager determines whether a window of the scanner is dirty or clean based on the sampled image.

In an embodiment, at 231, the scan window state manager compares a speckle counter value associated with the sampling against a threshold value to determine whether the window is dirty or clean. In an embodiment, the threshold value changes each time a clean window is processed for speckles and the threshold values represent an acceptable speckle count for a determined cleaned window.

Figure 3:
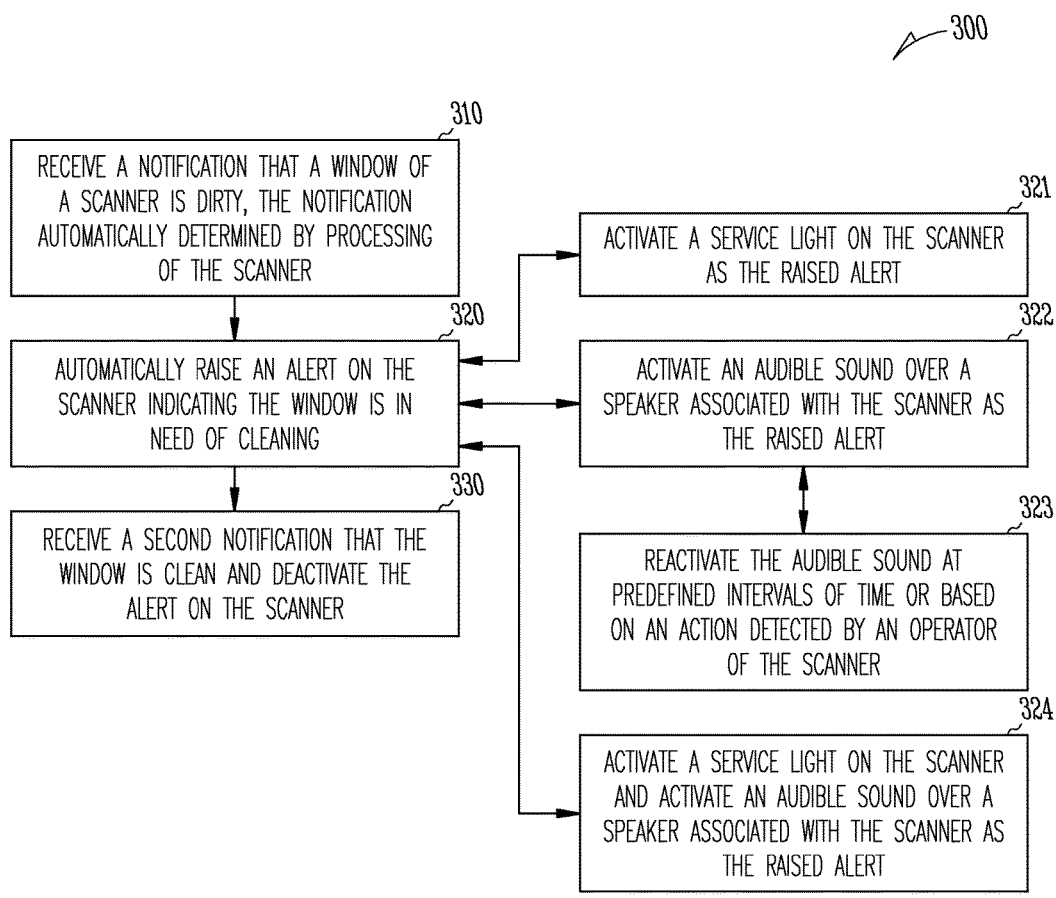
FIG. 3 is a diagram of another method for automatic alerting for a dirty/clean window of a scanner, according to an example embodiment.

FIG. 3 is a diagram of another method 300 for automatic alerting for a dirty/clean window of a scanner, according to an example embodiment. The software module(s) that implements the method 300 is referred to as a "scanner window alert manager." The scanner window alert manager is implemented as executable instructions programmed and residing within memory and/or a non-transitory computer-readable (processor-readable) storage medium and executed by one or more processors of a scanner. The processors that execute the scanner window alert manager are specifically configured and programmed to process the scanner window alert manager. The scanner window alert manager may or may not have access to one or more networks during its processing. Each network can be wired, wireless, or a combination of wired and wireless.

In an embodiment, the scanner that executes the scanner window alert manager is the scanner 110 of the FIG. 1.

In an embodiment, the scanner that executes the scanner window alert manager is a bar code scanner.

In an embodiment, the scanner is integrated into a checkout station operated by a cashier.

In an embodiment, the scanner is integrated into a self-service checkout station operated by a customer.

In an embodiment, the scanner window alert manager is the alert manager 144 of the FIG. 1.

At 210, the scanner window alert manager receives a notification that a window of a scanner is dirty. The notification automatically determined by processing of the scanner. In an embodiment, the notification comes from the scan window state manager of the FIG. 2. In an embodiment, the notification comes from the dirty/clean window detector 143 of the FIG. 1.

At 320, the scanner window alert manager automatically raises an alert on the scanner indicating the window is in need of cleaning for proper operation of the scanner. The alert can be raised in a number of manners.

For example, at 321, the scanner window alert manager activates a service light on the scanner as the raised alert.

In another case, at 322, the scanner window alert manager activates an audible sound over a speaker associated with the scanner as the raised alert.

In an embodiment of 322 and at 323, the scanner window alert manager reactivates the audible sound at predefined intervals of time or based on an action detected by an operator of the scanner. The action can be the start of a transaction at a POS system that informs the scanner to be ready, a swipe of a product at the POS system, and the like. The interval of time can be a configured item based on desires of an enterprise that services or uses the scanner.

In an embodiment, at 324, the scanner window alert manager activates a service light on the scanner and activates an audible sound over a speaker associated with the scanner as the raised alert. So, both a light activation and a sound activation can be the raised alert.

According to an embodiment, at 330, the scanner window alert manager receives a second notification that the window is clean and in response thereto deactivates the alert on the scanner.

Figure 4:
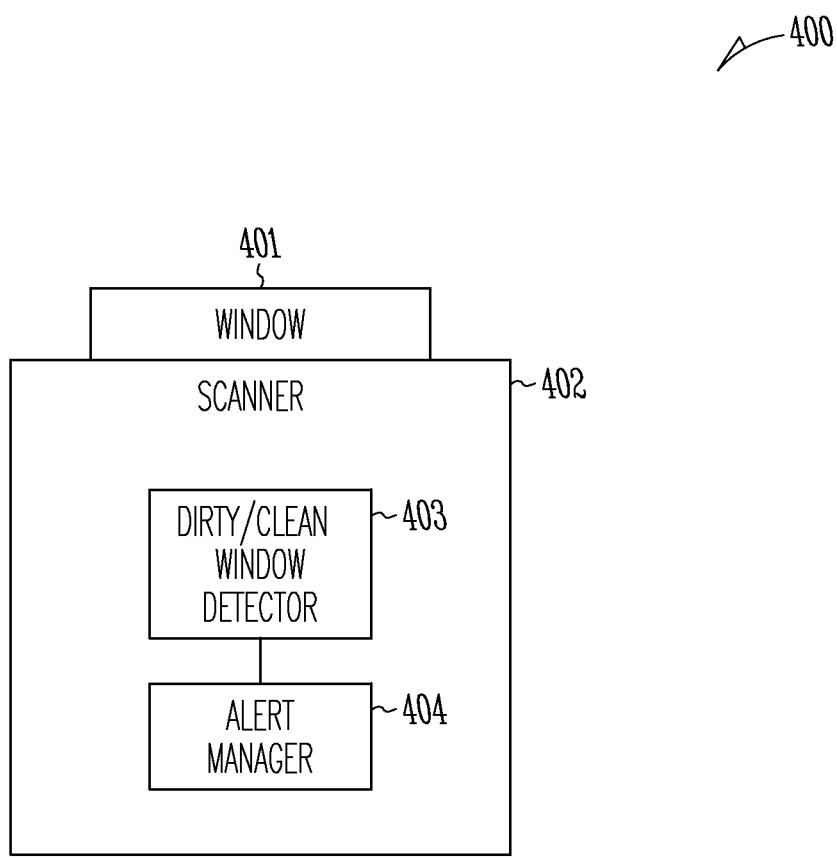
FIG. 4 is a diagram of a dirty/clean window detection system, according to an example embodiment.

FIG. 4 is a diagram of a dirty/clean window detection system 400, according to an example embodiment. Some components of the dirty/clean window detection system 400 are programmed and reside within memory and/or a non-transitory computer-readable medium and execute on one or more processors of the dirty/clean window detection system 400. The dirty/clean window detection system 400 may or may not communicate over one or more networks, which can be wired, wireless, or a combination of wired and wireless.

In an embodiment, the dirty/clean window detection system 400 is integrated into a checkout station operated by a cashier.

In an embodiment, the dirty/clean window detection system 400 is integrated into a self-service checkout station operated by a customer.

In an embodiment, the dirty/clean window detection system 400 during operation performs the processing associated with the FIGS. 1-3.

The dirty/clean window detection system 400 includes a window 401, a scanner 402, a dirty/clean window detector 403, and an alert manager 404.

The window 401 includes an outwardly facing side that is exposed to the environment where items (products or documents) are being scanned by the scanner 402. The outwardly facing side collects dirt and debris from the environment during the course of operating the scanner 402.

It is noted that multiple windows 401 may exists and that a single window 401 was presented for purposes of illustration only.

The scanner 402 includes a variety of components, such as a processor, memory, sensors, non-volatile and non-transitory storage, and others. The scanner 402 also includes as executable instructions implemented as software modules in the non-transitory storage: the dirty/clean window detector 403 and the alert manager 404.

In an embodiment, the scanner 402 is the scanner 110 of the FIG. 1.

In an embodiment, the scanner 402 is a bar code scanner.

The dirty/clean window detector 403 is adapted and configured to: execute on the scanner, obtain an image from the scanner 402, and determine whether the image is dirt or debris deposited on the window 401.

In an embodiment, the dirty/clean window detector 403 is the dirty/clean window detector 143 of the FIG. 1.

In an embodiment, the dirty/clean window detector 403 is the scan window state manager of the FIG. 2.

In an embodiment, the dirty/clean window detector 403 is further adapted and configured to use a speckle count for a clean window to compare against a second speckle count processed from the image to determine whether the window is dirty of clean.

The alert manager 404 is adapted and configured to: execute on the scanner 402, receive an indication from the dirty/clean window detector 403 as to whether the window 401 is dirty or clean, and turn on an alert when the window 401 is dirty and turn off the alert when the window 401 is clean.

In an embodiment, the alert manager 404 is the alert manager 144 of the FIG. 1.

In an embodiment, the alert manager 404 is the scanner window alert manager of the FIG. 3.

According to an embodiment, the alert manager 404 is further adapted and configured to turn off the alert when the dirty/clean window detector indicates the window is clean.

One now appreciates how a scanner can automatically detect when windows of the scanner are dirty or clean and automatically raise and turn off alerts. This ensures proper cleaning and operation of the scanner in a more efficient manner.

It should be appreciated that where software is described in a particular form (such as a component or module) this is merely to aid understanding and is not intended to limit how software that implements those functions may be architected or structured. For example, modules are illustrated as separate modules, but may be implemented as homogenous code, as individual components, some, but not all of these modules may be combined, or the functions may be implemented in software structured in any other convenient manner.

Furthermore, although the software modules are illustrated as executing on one piece of hardware, the software may be distributed over multiple processors or in any other convenient manner.

The above description is illustrative, and not restrictive. Many other embodiments will be apparent to those of skill in the art upon reviewing the above description. The scope of embodiments should therefore be determined with reference to the appended claims, along with the full scope of equivalents to which such claims are entitled.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate exemplary embodiment.

The invention claimed is:

1. A method, comprising:
    setting, by the scanner, a threshold value based on a detected clean window of the scanner;
    obtaining, by a scanner, an image, wherein obtaining further includes obtaining the image after inferring that the scanner is presently not in use based on a lack of activity being detected for: a non-zero stable weight that is detected on a weigh scale and readings from bar codes;
    down-sampling, by the scanner, the image by averaging each 2×2 block of pixels in the image into a single pixel creating a down-sampled image accounting for a resolution of the image;
    sampling, by the scanner, the down-sampled image for detection of dirt or debris by sampling 3×3 arrays of pixels from the down-sampled image by maintaining a current pixel at a center pixel of each 3×3 array of pixels and obtaining eight nearest neighboring pixels that surround the center pixel, wherein sampling further includes incrementing a speckle counter when a particular center pixel value is one of: less than a lowest value and greater than a highest value based on whether the image was captured using an external light source that is external to the scanner or an internal light source that is internal to the scanner; and determining, by the scanner, whether a window through which the image was obtained by the scanner is dirty or clean based on the sampled down-sampled image by comparing pixel values for the center pixels of each 3×3 array of pixels to each of that center pixel's eight nearest neighboring pixels, incrementing the speckle counter accordingly, and comparing a speckle counter value to the threshold value for determining whether the window of the scanner is dirty or clean.

2. The method of claim 1, wherein sampling further includes incrementing the speckle counter when a particular center pixel value is less than the lowest value and a predetermined constant value or when the particular center pixel value is more than the highest value and the predetermined value.

3. A system, comprising:
   a window;
   a scanner;
   a dirty/clean window detector adapted and configured to: i) execute on the scanner, ii) set a threshold value for a detected clean window of the scanner and obtain an image from the scanner when the scanner determines that there is a lack of activity on the scanner for: a non-zero stable weight that is detected on a weigh scale and readings from bar codes, and iii) determine whether the image contains dirt or debris deposited on the window by processing to: a) down-sample the image, averaging each 2×2 block of pixels in the image into a single pixel creating a down-sampled image accounting for a resolution of the image, b) sample 3×3 arrays of pixels from the down-sampled image by maintaining a current pixel at a center pixel of each 3×3 array of pixels and obtaining eight nearest neighboring pixels that surround the center pixel and comparing pixel values for the center pixels of each 3×3 array of pixels to each of that center pixel's eight nearest neighboring pixels, c) increment a speckle counter when a particular center pixel value is less than a lowest value or greater than a highest value based on whether the image was captured using an external light source that is external to the scanner or an internal light source that is internal to the scanner, and d) determine the window to be dirty when the speckle counter is greater than the threshold value set for the clean window; and
   an alert manager adapted and configured to: i) execute on the scanner, ii) receive an indication from the dirty/clean window detector as to whether the window is dirty or clean, and iii) turn on an alert when the window is dirty and turn off the alert when the window is clean.

4. The system of claim 3, wherein the dirty/clean window detector is further adapted in iii) for the dirty/clean window detector to use a clean speckle count for the clean window as the threshold value.

5. The system of claim 3, wherein the alert manager is further adapted and configured to turn off the alert when the dirty/clean window detector indicates the window is clean.

6. The system of claim 3, wherein the system is integrated into a checkout station, and the checkout station is one of cashier operated and customer operated, and the scanner is a bar code scanner.

* * * * *